(12) United States Patent
Kim et al.

(10) Patent No.: US 12,062,193 B2
(45) Date of Patent: Aug. 13, 2024

(54) APPARATUS FOR PREPROCESSING IMAGE DATA

(71) Applicant: DIO CORPORATION, Busan (KR)

(72) Inventors: Jin Cheol Kim, Busan (KR); Jin Baek Kim, Busan (KR)

(73) Assignee: DIO CORPORATION, Busan (KR)

( * ) Notice: Subject to any disclaimer, the term of this patent is extended or adjusted under 35 U.S.C. 154(b) by 198 days.

(21) Appl. No.: 17/602,617

(22) PCT Filed: Feb. 26, 2020

(86) PCT No.: PCT/KR2020/002755
§ 371 (c)(1),
(2) Date: Oct. 8, 2021

(87) PCT Pub. No.: WO2020/209495
PCT Pub. Date: Oct. 15, 2020

(65) Prior Publication Data
US 2022/0198686 A1 Jun. 23, 2022

(30) Foreign Application Priority Data

Apr. 11, 2019 (KR) .................. 10-2019-0042381
Apr. 11, 2019 (KR) .................. 10-2019-0042437

(51) Int. Cl.
*G06T 7/30* (2017.01)
*A61B 6/00* (2006.01)
(Continued)

(52) U.S. Cl.
CPC ............... *G06T 7/30* (2017.01); *A61B 6/032* (2013.01); *A61B 6/51* (2024.01); *A61B 6/5223* (2013.01);
(Continued)

(58) Field of Classification Search
CPC .............. G06T 7/30; G06T 17/205; G06T 2207/30036; G06T 2207/10081; A61B 6/5223; A61B 6/14
See application file for complete search history.

(56) References Cited

U.S. PATENT DOCUMENTS

| 6,338,000 B1 * | 1/2002 | Nakajima | ............... G06F 30/15 700/83 |
| 2006/0083422 A1 | 4/2006 | Ernst et al. | |

(Continued)

FOREIGN PATENT DOCUMENTS

| CN | 105046750 | 11/2015 |
| CN | 105551081 | 5/2016 |

(Continued)

OTHER PUBLICATIONS

Machine translated, KR-101655910. Date Published: Sep. 9, 2016. (Year: 2016).*

(Continued)

*Primary Examiner* — Sing-Wai Wu
(74) *Attorney, Agent, or Firm* — K&L Gates LLP

(57) ABSTRACT

The present invention provides an apparatus for preprocessing image data, comprising: a preprocessor for reducing a mesh resolution of an oral scan image to a reference resolution; a start line detector for detecting, from the preprocessed oral scan image, a start line corresponding to a bottom of a gum area; a boundary line detector for detecting, from the preprocessed oral scan image, a boundary line between a dental area and a gum area; and an area separator for separating a gum area from the oral scan image by using the start line and the boundary line.

15 Claims, 13 Drawing Sheets

(51) Int. Cl.
*A61B 6/03* (2006.01)
*A61B 6/51* (2024.01)
*G06T 17/20* (2006.01)

(52) U.S. Cl.
CPC .. *G06T 17/205* (2013.01); *G06T 2207/10081* (2013.01); *G06T 2207/30036* (2013.01)

(56) References Cited

U.S. PATENT DOCUMENTS

| | | | | |
|---|---|---|---|---|
| 2009/0213119 | A1* | 8/2009 | Oh | G06T 17/20 345/423 |
| 2016/0070821 | A1 | 3/2016 | Somasundaram et al. | |
| 2017/0132791 | A1* | 5/2017 | Li | G06T 19/20 |
| 2017/0169562 | A1* | 6/2017 | Somasundaram | G06V 10/26 |
| 2021/0322136 | A1* | 10/2021 | Anssari Moin | G16H 30/40 |

FOREIGN PATENT DOCUMENTS

| | | |
|---|---|---|
| CN | 106604692 | 4/2017 |
| CN | 105551081 | 4/2018 |
| KR | 20110138125 | 12/2011 |
| KR | 20140015239 | 2/2014 |
| KR | 101655910 | 9/2016 |
| KR | 20170127950 | 11/2017 |
| KR | 20180108797 | 10/2018 |
| KR | 101913586 | 11/2018 |
| KR | 101953341 | 3/2019 |
| KR | 20190024360 | 3/2019 |
| WO | 20160108453 | 7/2016 |

OTHER PUBLICATIONS

Wu et al., "Tooth segmentation on dental meshes using morphologic skeleton", Computers & Graphics 38 (2014) p. 199-211. (Year: 2014).*

Office Action issued to related European Application No. 20786737.5, dated Jan. 3, 2023, 8 pages.

Office Action issued to related CN Application No. 202080027597.2., dated Jan. 19, 2024, 11 pages (with English translation).

* cited by examiner (a)

(b)

(a)

(b)

(a)

(b)

APPARATUS FOR PREPROCESSING IMAGE DATA

PRIORITY CLAIM AND CROSS-REFERENCE TO RELATED APPLICATIONS

This application is a 371 application of PCT/KR2020/002755, filed on Feb. 26, 2020, which claims priority to and the benefit of Korean Patent Application Nos. 10-2019-0042381 and 10-2019-0042437, filed on Apr. 11, 2019, the disclosures of which are incorporated herein by reference in their entirety.

BACKGROUND

1. Field of the Invention

The present invention relates to an apparatus for preprocessing image data, and more particularly, to an apparatus for separating and removing elements that interfere with image registration of an oral scan image and a dental CT image from the oral scan image and the dental CT image before image registration.

2. Discussion of Related Art

In the field of computer vision, when the same subject is photographed from different times, measurement methods, or viewpoints, etc., images having different coordinate systems are obtained, and image registration refers to processing for displaying these different images in one coordinate system.

In particular, in the field of dentistry, image registration is performed between a dental CT image and an oral scan image before a procedure such as an implant. In this case, the registered image can be used as important data for determining the optimal implant operation position by allowing the location of the bone tissue and neural tube to be identified.

However, the oral scan image includes an unnecessary area during image registration with the CT image. In particular, there is a problem in that unnecessary areas, such as the gum area and the dental root area, may become an interference element in image registration, thereby reducing the time, accuracy, and efficiency of image registration.

SUMMARY OF THE INVENTION

The present invention is directed to providing an apparatus for separating and removing a gum area and a dental root area, which are elements that interfere with image registration of an oral scan image and a dental CT image from the oral scan image and the CT image before image registration.

The technical problems to be solved in the present invention are not limited to the technical problems mentioned above, and other technical problems not mentioned will be clearly understood by those of ordinary skill in the art from the following description.

The present invention provides an apparatus for preprocessing image data, comprising: a preprocessor for reducing a mesh resolution of an oral scan image to a reference resolution; a start line detector for detecting, from the preprocessed oral scan image, a start line corresponding to a bottom of a gum area; a boundary line detector for detecting, from the preprocessed oral scan image, a boundary line between a dental area and a gum area; and an area separator for separating a gum area from the oral scan image by using the start line and the boundary line.

Here, the start line detector calculates the number of adjacent vertexes for each mesh of the oral scan image, selects vertexes having the calculated number of vertexes equal to or less than a reference number, and detects the start line by connecting the selected vertexes.

In addition, the start line detector calculates a curvature of each mesh of the oral scan image, selects meshes having the calculated curvature equal to or less than a reference curvature, and detects the start line by connecting the vertexes included in the selected meshes.

In addition, the boundary line detector calculates a curvature between adjacent meshes of the oral scan image, selects meshes having the calculated curvature equal to or greater than a reference curvature, and determines a vertex shared by the selected meshes as a boundary point.

In addition, the boundary line detector calculates a maximum curvature and a minimum curvature between adjacent meshes of the oral scan image, and calculates at least one of a Gaussian curvature and an average curvature by using the calculated maximum and minimum curvatures.

In addition, the boundary line detector selects meshes having at least any one of the calculated Gaussian curvature and the average curvature equal to or greater than a reference curvature, and determines a vertex shared by the selected meshes as a boundary point.

In addition, the boundary line detector connects the adjacent boundary points by sequentially dilating and eroding the boundary points.

In addition, the boundary line detector labels each of the connected boundary points with the same label.

In addition, the boundary line detector dilates at least once for each labeled label, and integrates adjacent labels.

In addition, the apparatus for preprocessing image data of the present invention may further include an area setting unit for integrating vertexes connected from the start line to the boundary line and setting it as a separation target area.

In addition, the apparatus for preprocessing image data of the present invention may further include a reference line determination unit for determining the outermost line of the separation target area as a separation reference line for separating a gum area from the oral scan image.

In addition, the area separator separates a gum area from the oral scan image using the separation reference line.

In addition, the apparatus for preprocessing image data of the present invention may further include a reference plane extraction unit for extracting a reference plane from a CT image; an area setting unit for setting an area spaced apart by a predetermined height from the reference plane as a dental root area; and an image processing unit for processing the CT image data so that the dental root area is removed from the CT image.

Here, the reference plane extraction unit may set a plane at heights of the maxillary outermost teeth or at a height spaced apart from it by a predetermined height as a reference plane for the maxilla, and set a plane at heights of the mandibular outermost teeth or at a height spaced apart from it by a predetermined height as a reference plane for the mandible, respectively.

In addition, the reference plane extraction unit may extract a three-dimensional boundary surface that is located in a space between the maxillary teeth and the mandibular teeth and reflects heights of the maxillary teeth and the mandibular teeth, as a reference plane.

In addition, the reference plane extraction unit may set a three-dimensional boundary surface corresponding to a shape of ends of maxillary teeth as a reference plane for the maxilla, and a three-dimensional boundary surface corresponding to a shape of ends of mandibular teeth as a reference plane for the mandible, respectively.

The present invention configured as described above has useful benefits that it makes it possible to easily separate and remove the gum area and dental root area, which are elements that interfere with image registration of oral scan images and dental CT images, before image registration, thereby reducing the time, accuracy, and efficiency of image registration.

BRIEF DESCRIPTION OF THE DRAWINGS

The above and other aspects, features, and advantages of the present invention will become more apparent to those of ordinary skill in the art by describing embodiments thereof in detail with reference to the accompanying drawings, in which.

DETAILED DESCRIPTION OF EXEMPLE EMBODIMENTS

Figure 1:
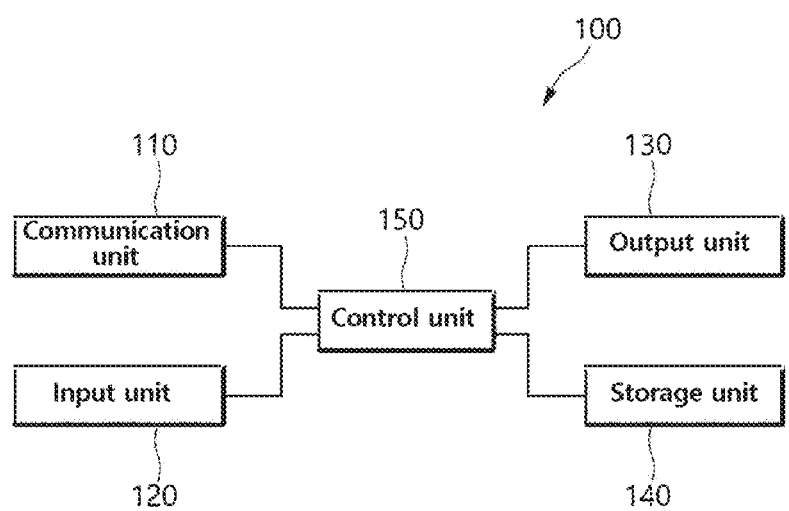
FIG. 1 is a block diagram showing a main configuration of an apparatus for preprocessing image data according to an exemplary embodiment of the present invention.

The present invention and method of accomplishing the same may become more apparent through the following detailed description in relation to the accompanying drawings, and accordingly, those of ordinary skill in the art will be able to easily implement the technical idea of the present invention. In addition, in describing the present invention, when it is determined that a detailed description of a related known technology may unnecessarily obscure the subject matter of the present invention, the detailed description will be omitted.

The terms used in this specification are for the purpose of describing embodiments only and are not intended to be limiting to the present invention. In this specification, the singular form also includes the plural form in some cases, unless specifically specified in the phrase. In this specification, terms such as "include", "comprise", "provide" or "have" do not exclude the presence or addition of one or more other elements other than elements mentioned.

In this specification, terms such as "or" and "at least one" may represent one of the words listed together or a combination of two or more. For example, "A or B" and "at least one of A and B" may include only one of A or B, or may also include both A and B.

In this specification, descriptions according to "for example", etc. may not exactly match the information presented, such as the recited properties, variables, or values, and effects such as modifications, including tolerances, measurement errors, limits of measurement accuracy, and other commonly known factors should not limit the modes for carrying out the invention according to the various exemplary embodiments of the present invention.

In this specification, when an element is described as being "connected" or "linked" to another element, it will be understood that it may be directly connected or linked to the other element but intervening elements may also be present. On the other hand, when an element is referred to as being "directly connected" or "directly linked" to another element, it will be understood that there are no intervening elements present.

In this specification, when an element is described as being "on" or "adjacent to" another element, it will be understood that it may be directly "on" or "connected to" the other element but intervening elements may also be present. On the other hand, when an element is described as being "directly on" or "directly adjacent to" another element, it will be understood that there are no intervening elements present. Other expressions describing the relationship between the elements, for example, 'between' and 'directly between', and the like can be interpreted similarly.

In this specification, terms such as "first" and "second" may be used to describe various elements, but, the above elements should not be limited by the terms above. In addition, the above terms should not be construed as limiting the order of each component, and may be used for the purpose of distinguishing one element from another. For example, "first element" may be named as "second element" and similarly, "second element" may also be named as "first element."

Unless otherwise defined, all terms used in this specification may be used with meanings commonly understood by those of ordinary skill in the art. In addition, terms defined in a commonly used dictionary are not interpreted ideally or excessively unless explicitly and specifically defined.

Hereinafter, a preferred embodiment according to the present invention will be described in detail with reference to the accompanying drawings.

The apparatus for preprocessing image data according to an exemplary embodiment of the present invention is an electronic apparatus for removing elements that interfere with image registration of an oral scan image and a CT image before image registration, and may be divided into a configuration for preprocessing an oral scan image and a configuration for preprocessing a CT image. First, the configuration for preprocessing the oral scan image will be described first, and then the configuration for preprocessing the CT image will be described.

Figure 2:
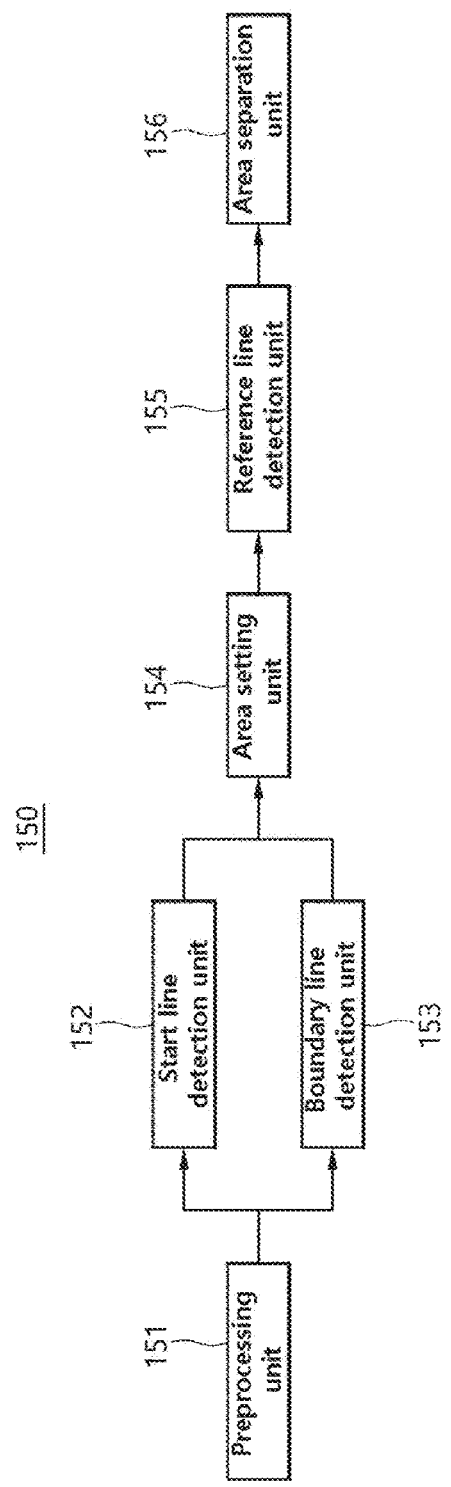
FIG. 2 is a detailed block diagram of a configuration for preprocessing an oral scan image of a controller of FIG. 1.

FIG. 1 is a block diagram showing a main configuration of an apparatus for preprocessing image data according to an exemplary embodiment of the present invention, and FIG. 2 is a detailed block diagram of a configuration for preprocessing an oral scan image of a controller of FIG. 1.

Referring to FIG. 1, the apparatus 100 for preprocessing image data according to an exemplary embodiment of the present invention may include a communicator 110, an input unit 120, a display unit 130, a storage 140, and a controller 150 in order to separate and remove a gum area and a dental root area that interfere with image registration of an oral scan image and a dental CT image from the oral scan image and the CT image, respectively.

The communicator 110 communicates with an external device such as an image photographing device (not shown) and a server (not shown). It may receive image data for the inside of the oral cavity. For example, the communicator 110 may perform wireless communication such as 5th generation communication (5G), long term evolution-advanced (LTE-A), long term evolution (LTE), Bluetooth, Bluetooth low energy (BLE), and near field communication (NFC), and may perform wired communication such as cable communication.

In this case, the image data may include, in addition to the oral scan image and CT image data, other image data measured by a different measurement method for the inside of the oral cavity of the recipient. For example, the other image data may include magnetic resonance image data and the like. In this case, the CT image and the magnetic resonance image are three-dimensional images that display the internal state of the teeth, while the oral scan image is a three-dimensional image that displays the surface state of the teeth.

The CT image is an image taken through a computed tomography (CT) device using radiation. That is, the CT image may represent information on the distribution of internal tissues such as the dental crown, dental root, and alveolar bone in the oral cavity and bone density information based on the transmittance of the radiation.

The oral scan image is an image that provides information on the shape of the dental crown portion of the tooth exposed to the outside and the shape of the gum around the tooth. In this case, the oral scan image may be obtained by directly scanning the inside of the recipient's oral cavity through an oral scanner or may be obtained by scanning an impression model that mimics the inside of the recipient's oral cavity with an intaglio or a plaster model created through embossing of the impression model, and the scan image of the impression model can be inverted and used as an oral scan image.

The input unit 120 generates input data in response to a user input of the electronic apparatus 100. The input unit 120 includes at least one input means. The input unit 120 may include a keyboard, a keypad, a dome switch, a touch panel, a touch key, a mouse, a menu button, and the like.

The display unit 130 displays display data according to the operation of the electronic apparatus 100. The display unit 130 may include a liquid crystal display (LCD), a light emitting diode (LED) display, an organic light emitting diode (OLED) display, a micro electro mechanical systems (MEMS) display, and an electronic paper display. The display unit 130 may be combined with the input unit 120 to be implemented as a touch screen.

The storage 140 stores operation programs of the electronic apparatus 100. The storage 140 may store an algorithm necessary for separating a gum area from an oral scan image, such as a decimation algorithm, a floor detection algorithm, a morphological operation algorithm, and a grouping algorithm, and an algorithm necessary for separating the dental root area from a CT image. In addition, the storage 140 may store a plurality of image data received from an image photographing device or the like.

The controller 150 receives an oral scan image and a CT image from an external device such as an image photographing device and a server, separates and removes the gum area from the oral scan image, and separates and removes the dental root area from the CT image.

As described above, the apparatus 100 for preprocessing image data according to an exemplary embodiment of the present invention can improve the registration speed and accuracy by accurately separating and removing the gum area from the oral scan image and registering it and the dental CT image.

To this end, as shown in FIG. 2, the controller 150 may include a preprocessor 151, a start line detector 152, a boundary line detector 153, an area setting unit 154, a reference line determination unit 155, and an area separator 156.

Figure 3:
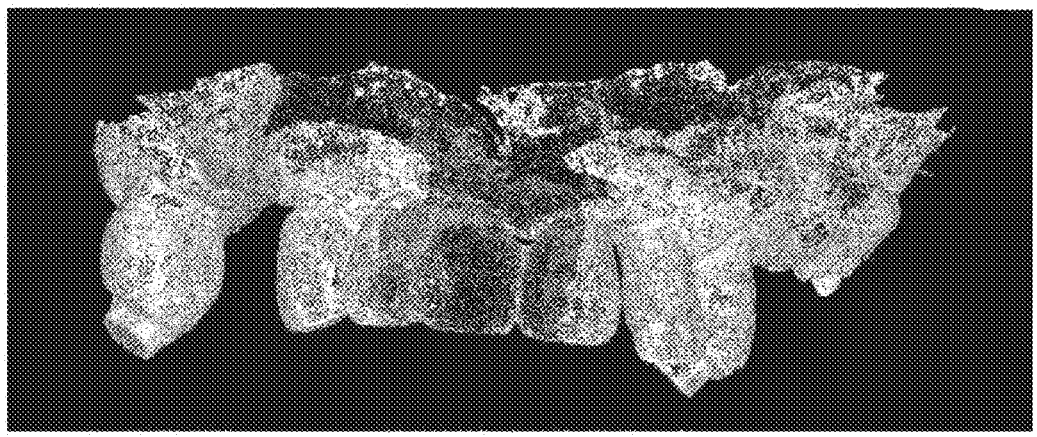
FIG. 3 is a view illustrating before and after preprocessing of an oral scan image according to an exemplary embodiment of the present invention.
Figure 3:
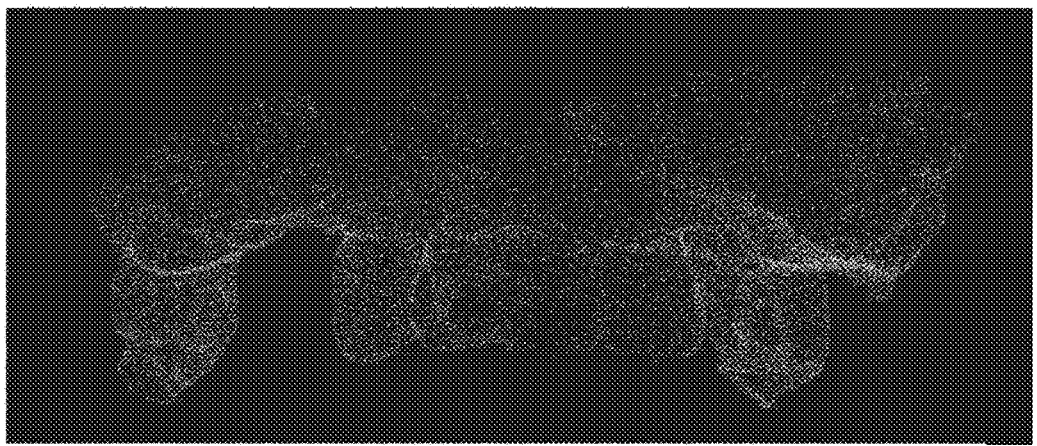

FIG. 3 is a view illustrating before and after preprocessing of an oral scan image according to an exemplary embodiment of the present invention.

The preprocessor 151 serves to lower the mesh resolution of the oral scan image to a reference resolution (e.g., 40,000 meshes). For example, the preprocessor 151 may reduce the number of meshes by using a decimation algorithm that reduces the number of data dimensions.

As shown in FIG. 3 (a), there is a problem in that in general, an oral scan image photographed by an image photographing device has a non-uniform distribution of mesh information and a relatively large number of meshes of 40,000 to 800,000, which takes a long time to process the mesh information.

However, as shown in FIG. 3 (b), when the preprocessor 151 according to an exemplary embodiment of the present invention reduces the number of meshes to 40,000 by using the decimation algorithm, the distribution of mesh information becomes uniform, and the processing speed of mesh information can be improved. However, since most features disappear when the number of meshes is excessively reduced, it is preferable to reduce the number to an appropriate number.

Figure 4:
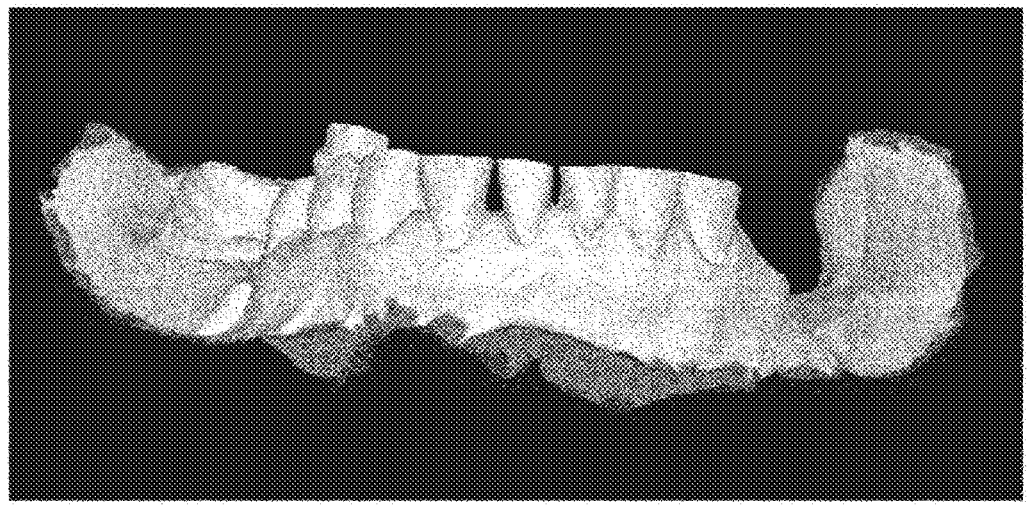
FIG. 4 is a view illustrating a start line detected in an oral scan image according to an exemplary embodiment of the present invention.
Figure 4:
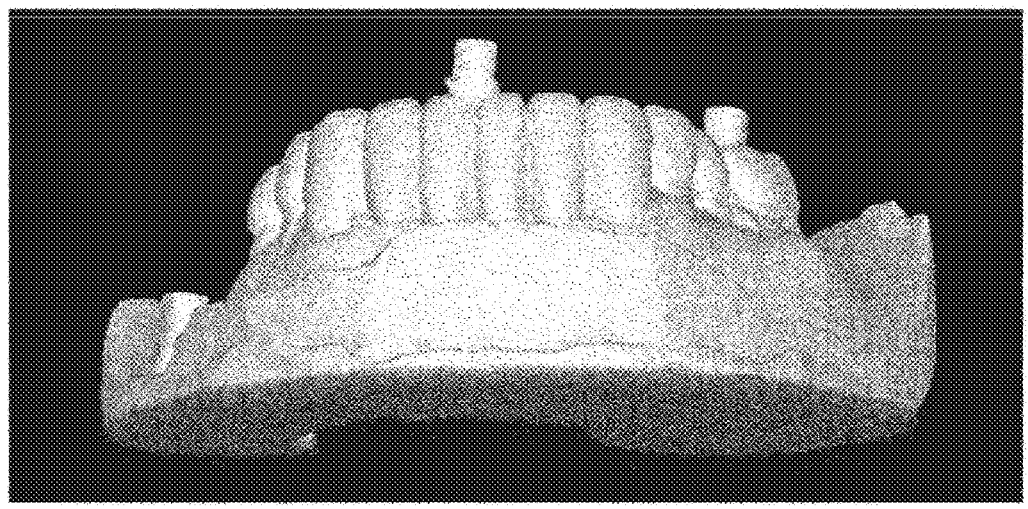

FIG. 4 is a view illustrating a start line detected in an oral scan image according to an exemplary embodiment of the present invention.

The start line detector 152 detects a start line that is a set of vertexes corresponding to a bottom of the gum area in the oral scan image preprocessed by the preprocessor 151. For example, the start line detector 152 may detect the start line using a Floor Detection algorithm.

Hereinafter, a method for the start line detector 152 to detect the start line will be described, but it is natural that the start plane can be detected by extending this.

Meanwhile, the oral scan image is divided into a hand type and a desk type, depending on an image photographing device that has photographed the image. Here, as shown in FIG. 4 (a), the hand type has an open bottom of the oral scan image, while the desk type has a flat bottom surface with the bottom of the oral scan image blocked as shown in FIG. 4 (*b*). Therefore, a method of detecting the start line is different depending on the type of the oral scan image.

Specifically, in the case of a hand-type oral scan image, since the bottom is open, the meshes corresponding to the bottom have a relatively small number of vertexes adjacent thereto. Based on this, first, the start line detector 152 calculates the number of adjacent vertexes for each mesh of the oral scan image, and selects vertexes having the calculated number of vertexes equal to or less than a reference number (e.g., 3). Next, the start line is detected by connecting the selected vertexes.

On the other hand, in the case of a desk-type oral scan image, since the bottom surface is flat, meshes with a relatively small curvature are highly likely to correspond to the bottom. Based on this, first, the start line detector 152 calculates a curvature of each mesh of the oral scan image, and selects meshes having the calculated curvature equal to or less than a reference curvature. Next, the start line is detected by connecting the vertexes included in the selected meshes.

The boundary line detector 153 detects boundary lines between the dental area and the gum area from the oral scan image preprocessed by the preprocessor 151.

Figure 5:
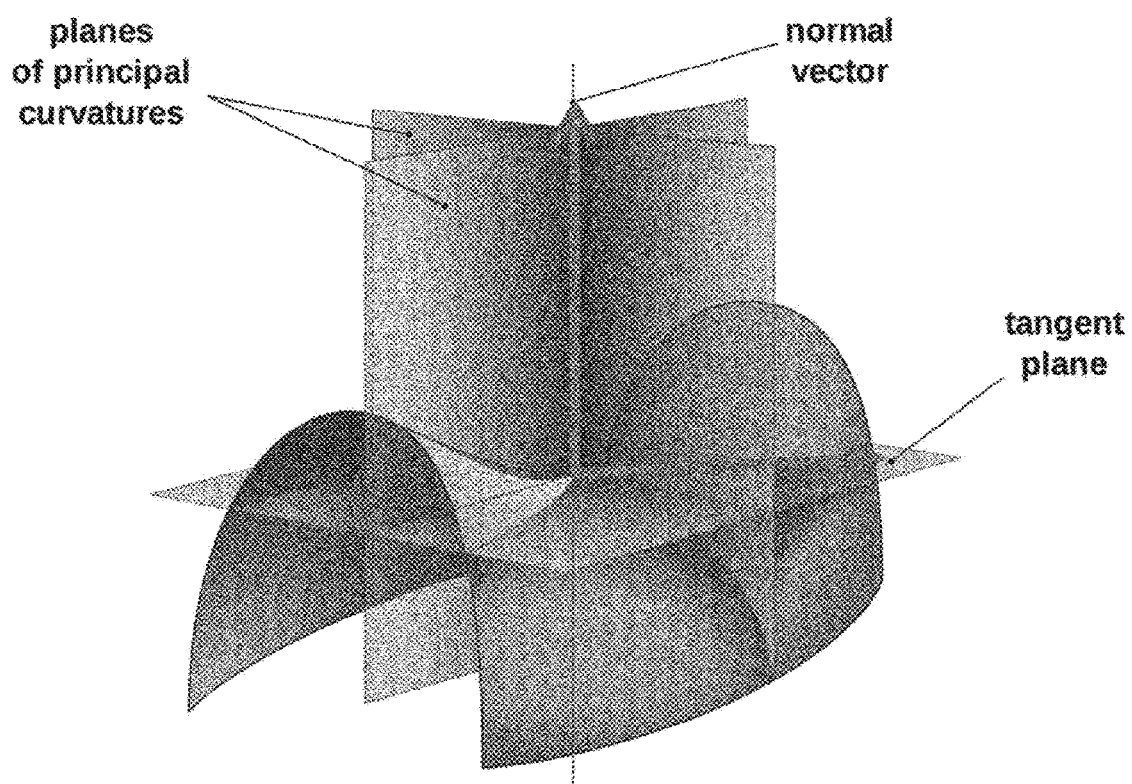
FIG. 5 is a view for explaining a method of calculating a curvature between adjacent meshes of an oral scan image according to an exemplary embodiment of the present invention.
Figure 6:
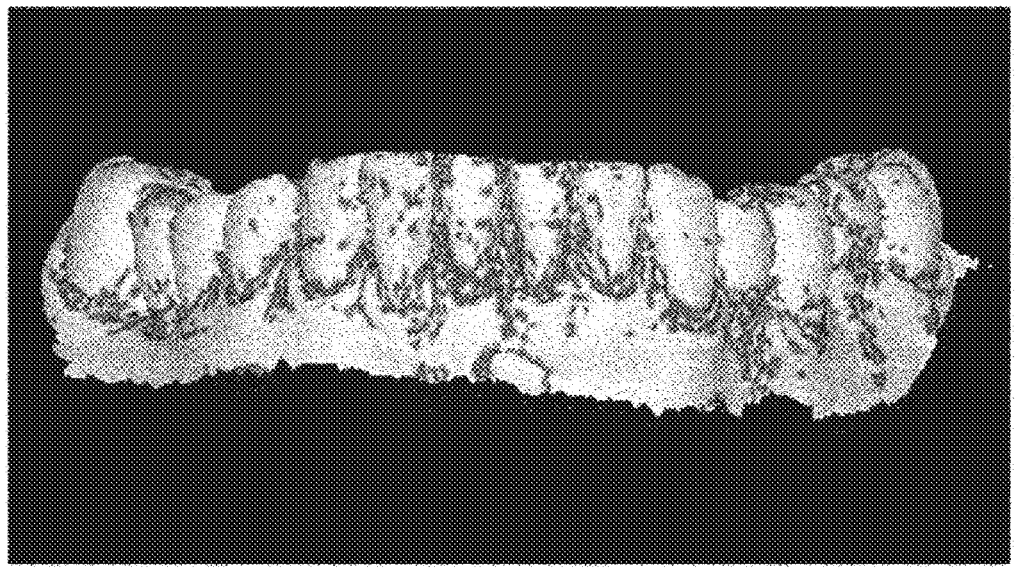
FIG. 6 is a view illustrating boundary points in an oral scan image.
Figure 6:
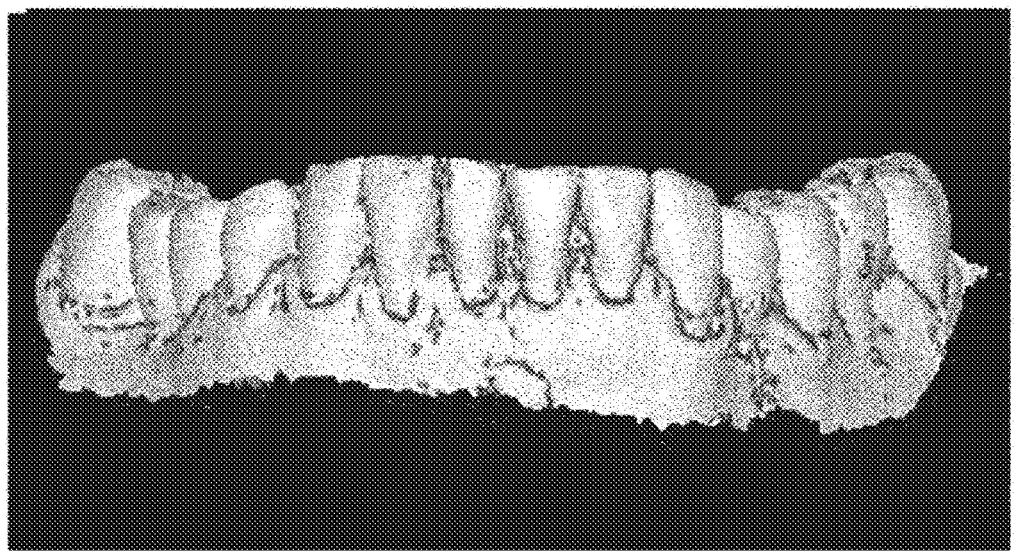

FIG. 5 is a view for explaining a method of calculating a curvature between adjacent meshes of an oral scan image according to an exemplary embodiment of the present invention and FIG. 6 is a view illustrating boundary points in an oral scan image.

The boundary line detector 153 calculates a curvature between adjacent meshes of the oral scan image, selects meshes having the calculated curvature equal to or greater than a reference curvature, and determines a vertex shared by the selected meshes as a boundary point.

Specifically, referring to FIGS. 5 and 6, the boundary line detector 153 calculates a maximum curvature and a minimum curvature between adjacent meshes of the oral scan image, and calculates at least one of a Gaussian curvature and an average curvature by using the calculated maximum and minimum curvatures. And, it selects meshes having at least any one of the calculated Gaussian curvature and the average curvature equal to or greater than a reference curvature, and determines a vertex shared by the selected meshes as a boundary point.

Here, it can be seen that the boundary points extracted using the Gaussian curvature and the average curvature (see FIG. 6 (*b*)) are more distinct than the boundary points extracted using the Gaussian curvature (see FIG. 6 (*a*)), so in terms of complementarity, it is preferable to determine the boundary point using both the Gaussian curvature and the average curvature.

Hereinafter, a method of extracting a boundary point from an oral scan image will be described with reference to FIG. 5.

The boundary line detector 153 draws, at a vertex shared by adjacent meshes, a plane that includes a normal vector and intersects the mesh curved surface, and then continues to intersect the plane with the mesh curved surface while rotating the plane around the normal vector. In this case, a number of curves centered on the vertex may be obtained on the mesh curved surface, and each curvature may be calculated using the angle between these curves and the tangent plane of the vertex. In addition, the largest value among these curvatures may be defined as the maximum curvature, and the smallest value may be defined as the minimum curvature. Meanwhile, a plane including two curves each having the largest maximum curvature and the smallest minimum curvature at the vertex among the calculated curvatures may be defined as a plane of principal curvatures.

Here, the Gaussian curvature is defined as the product of the maximum curvature and the minimum curvature, and the average curvature is defined as the average of the maximum curvature and the minimum curvature.

By selecting meshes having at least any one of the Gaussian curvature and the average curvature calculated in this way equal to or greater than a reference curvature, a vertex shared by the selected meshes is determined as a boundary point.

Figure 7:
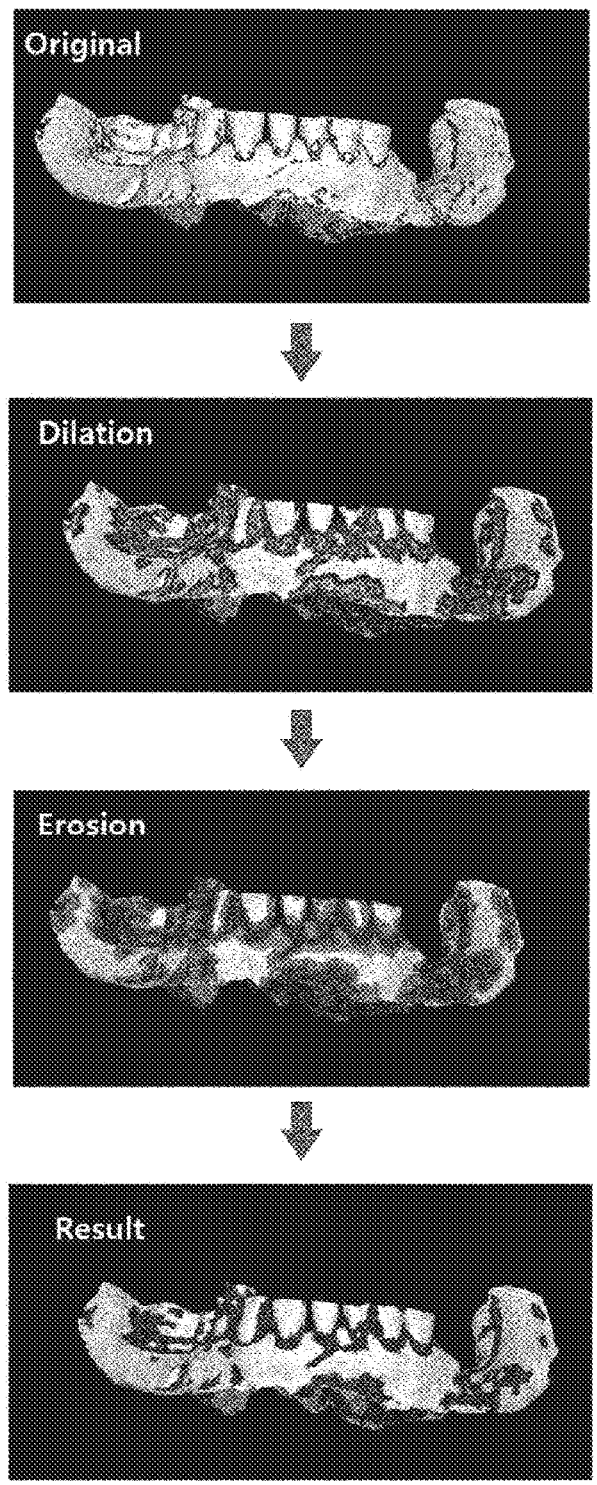
FIG. 7 is a view for explaining a method of connecting boundary points in an oral scan image according to an exemplary embodiment of the present invention.

FIG. 7 is a view for explaining a method of connecting boundary points in an oral scan image according to an exemplary embodiment of the present invention.

As shown in FIG. 7, the boundary line detector 153 connects adjacent boundary points by sequentially dilating and eroding boundary points using a morphological operation algorithm.

Here, the morphological operation algorithm is an algorithm for dilating and eroding an area, and is generally used for connecting or disconnecting adjacent points.

In this way, when the boundary points are dilated and then subjected to an erosion process, the boundary property between the tooth and the gum areas can be further improved because only the connection between adjacent boundary points is performed while maintaining the thickness of the existing boundary point component.

Figure 8:
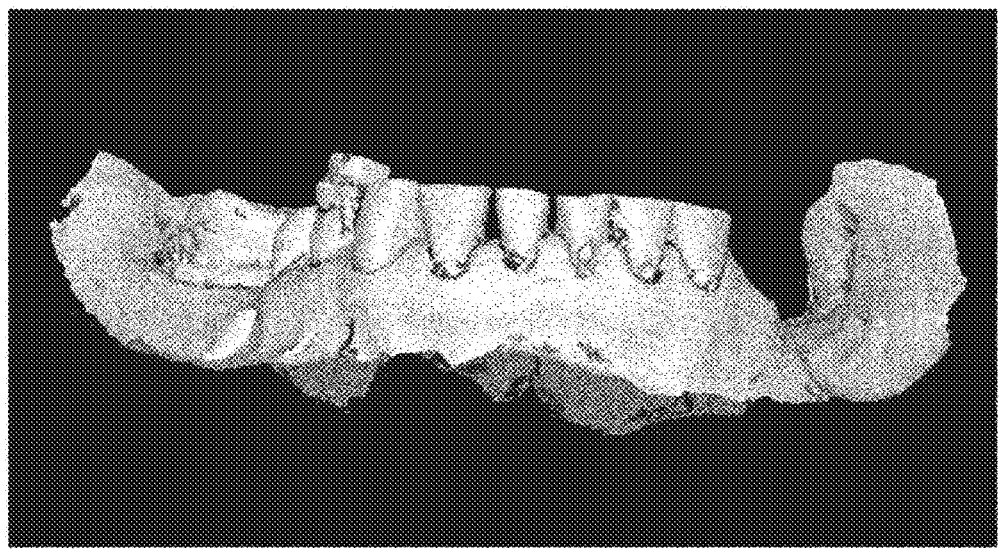
FIG. 8 is a view illustrating an oral scan image labeled with the same label for each of the connected boundary points.
Figure 9:
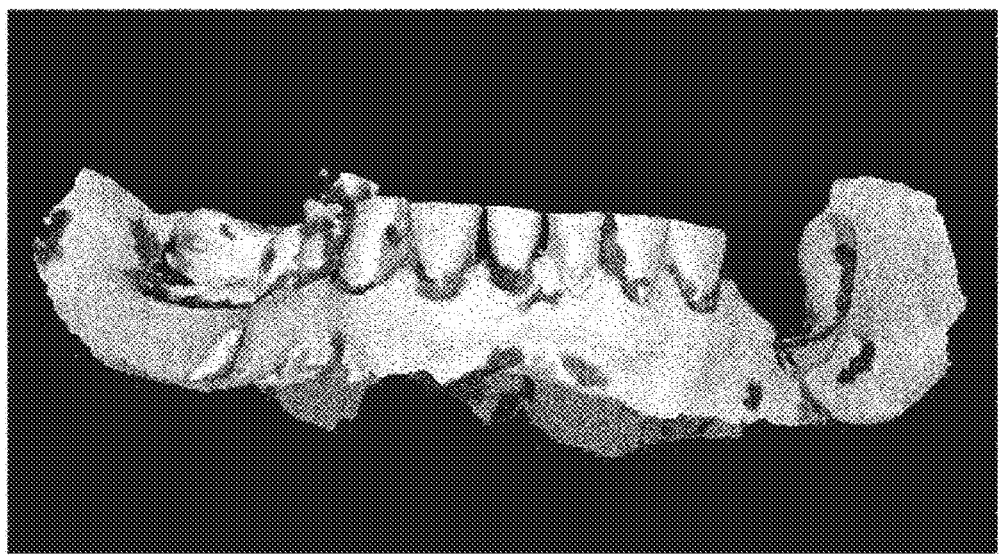
FIG. 9 is a view illustrating an area-dilated oral scan image for each label.
Figure 10:
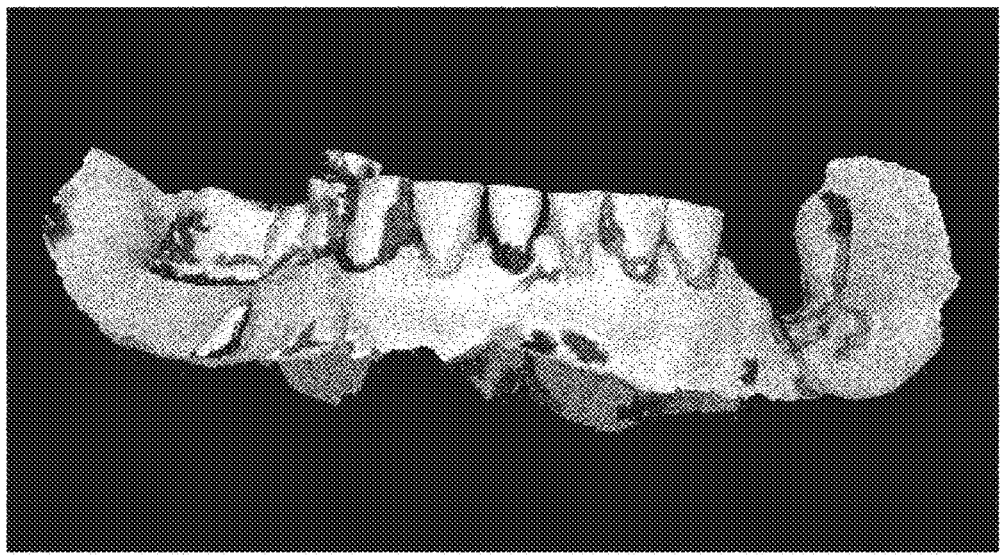
FIG. 10 is a view illustrating an oral scan image in which an area-dilated label is integrated.

FIG. 8 is a view illustrating an oral scan image labeled with the same label for each of the connected boundary points, FIG. 9 is a view illustrating an area-dilated oral scan image for each label, and FIG. 10 is a view illustrating an oral scan image in which an area-dilated label is integrated.

Referring to FIG. 8, the boundary line detector 153 labels each of the connected boundary points with the same label. In FIG. 8, different colors were displayed for each label.

Referring to FIGS. 9 and 10, the boundary line detector 153 dilates at least once for each labeled label, and integrates adjacent labels. Here, the dilation may be repeated until all labels are integrated. Accordingly, the boundary line can be labeled with one integrated label.

Figure 11:
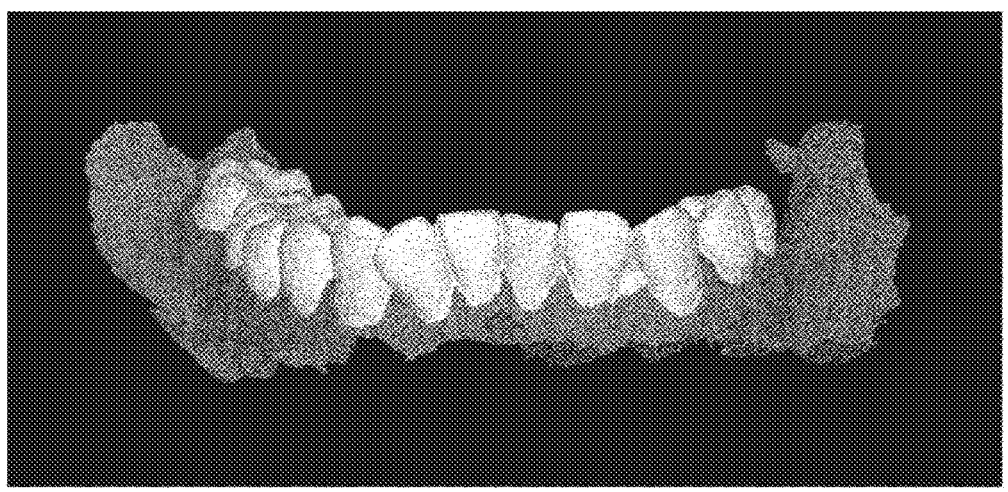
FIG. 11 is a view for explaining a method of setting a separation target area in an oral scan image according to an exemplary embodiment of the present invention.
Figure 12:
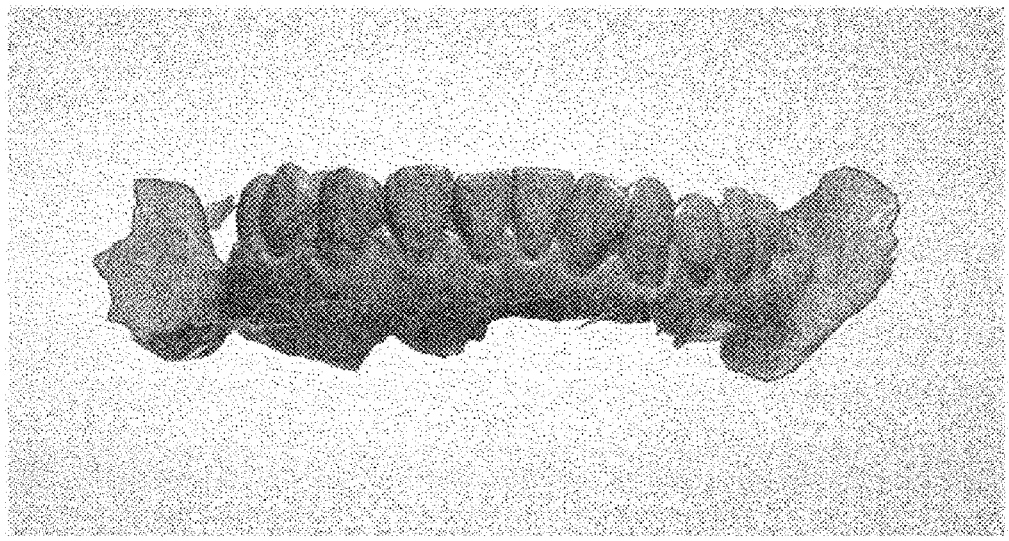
FIG. 12 is a view illustrating an oral scan image in which a separation reference line is indicated.
Figure 13:
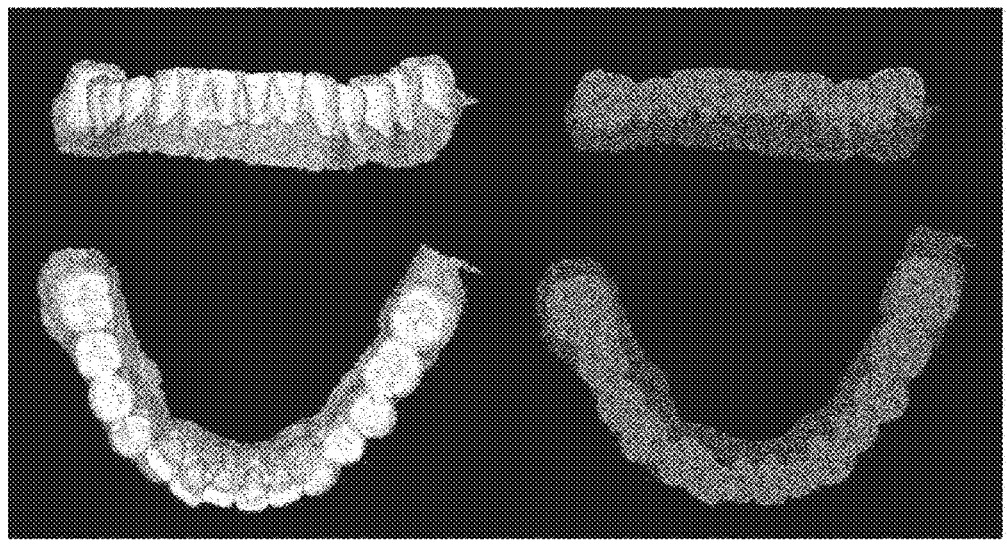
FIG. 13 is a view illustrating an oral scan image in which tooth and gum areas are separated based on a separation reference line.

FIG. 11 is a view for explaining a method of setting a separation target area in an oral scan image according to an exemplary embodiment of the present invention, FIG. 12 is a view illustrating an oral scan image in which a separation reference line is indicated, and FIG. 13 is a view illustrating an oral scan image in which tooth and gum areas are separated based on a separation reference line.

Referring to FIG. 11, the area setting unit 154 sets a gum area, which is a separation target area, based on the previously detected start line and boundary line. That is, the area setting unit 154 sequentially integrates vertexes connected from the start line to the boundary line and set it as the separation target area.

Referring to FIG. 12, the reference line determination unit 155 determines the outermost line of the separation target area as a separation reference line for separating a gum area from the oral scan image.

Referring FIG. 13, the area separator 156 separates a gum area from the oral scan image using the separation reference line.

As described above, the apparatus 100 for preprocessing image data according to an exemplary embodiment of the present invention can improve the registration speed and accuracy by relatively quickly and accurately separating and removing the gum area from the oral scan image and registering it and the dental CT image.

Hereinafter, a method for preprocessing CT image data according to an exemplary embodiment of the present invention controlled and operated by the controller 150 will be described.

Figure 14:
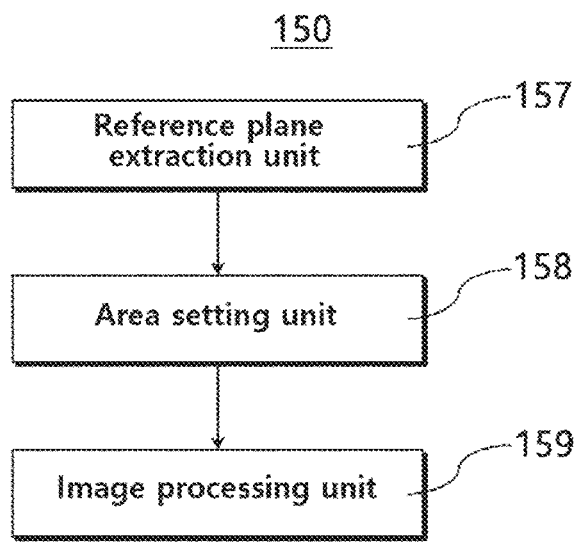
FIG. 14 is a detailed block diagram of a configuration for preprocessing a CT image of a controller of FIG. 1.

FIG. 14 is a detailed block diagram of a configuration for preprocessing a CT image of a controller of FIG. 1.

Referring to FIG. 14, the controller 150 according to an exemplary embodiment of the present invention may include a reference plane extraction unit 157, an area setting unit 158, and an image processing unit 159 to preprocess the CT image data.

The reference plane extraction unit 157 extracts a reference plane RP from the CT image.

The reference plane RP is a reference plane for setting the dental root area RA, which is the root area of the tooth, and may be a plane RP1 or a three-dimensional boundary surface RP2 having a curved shape. In addition, one reference plane RP may be extracted to be equally applied to the maxilla and the mandible, or two or more may be extracted to be applied to each of the maxilla and the mandible.

The area setting unit 158 sets an area spaced apart by a predetermined height from the reference plane RP as the dental root area RA of the CT image.

The dental root area RA is an unnecessary area of a CT image that is not included in other images, such as an oral scan image, and is an area that can reduce the time and efficiency of image registration by acting as an interference element in image registration between the CT image and the oral scan image. Accordingly, which part of the dental root area RA is in the CT image may be set at S202. However, when the dental root area RA is precisely set, the load for the setting operation may increase, so it may be desirable to set the dental root area RA roughly according to the method described above or later.

The image processing unit 159 processes the CT image data so that the dental root area RA set by the area setting unit 158 is removed from the CT image. That is, data corresponding to the dental root area RA may be removed from the CT image data.

As a result of preprocessing the CT image data, the CT image from which the dental root area RA has been removed may be used for image registration with other images according to various algorithms. In addition, after image registration according to these various algorithms is completed, by adding the removed dental root area RA to the corresponding CT image, a CT image and other images on which complete image registration has been performed may be derived.

Hereinafter, more detailed operations of the reference plane extraction unit 157 and the area setting unit 158 according to the type of the reference plane RP will be described. However, the reference plane (RP) and the preprocessing example are shown only for the mandible, but the present invention is not limited thereto, and the same method as for the mandible can be applied to the maxilla.

Figure 15:
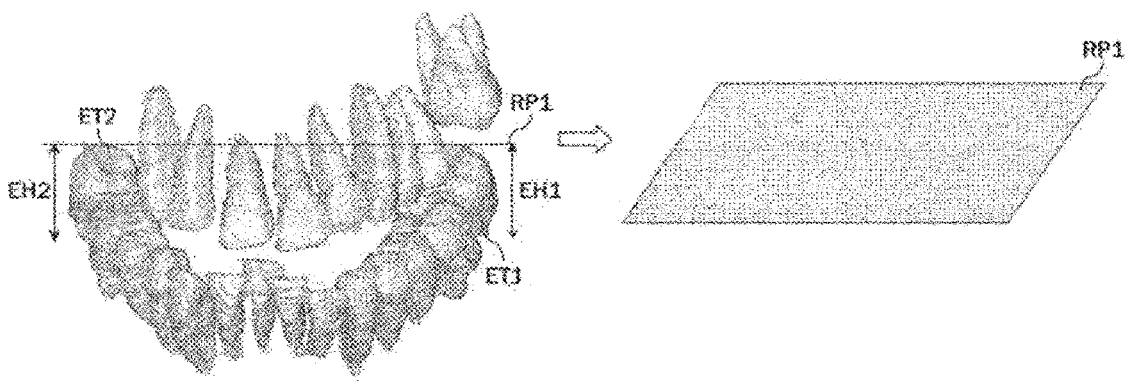
FIGS. 15 and 16 are exemplary views for explaining a preprocessing method when a flat reference plane RP1 is applied.
Figure 16:
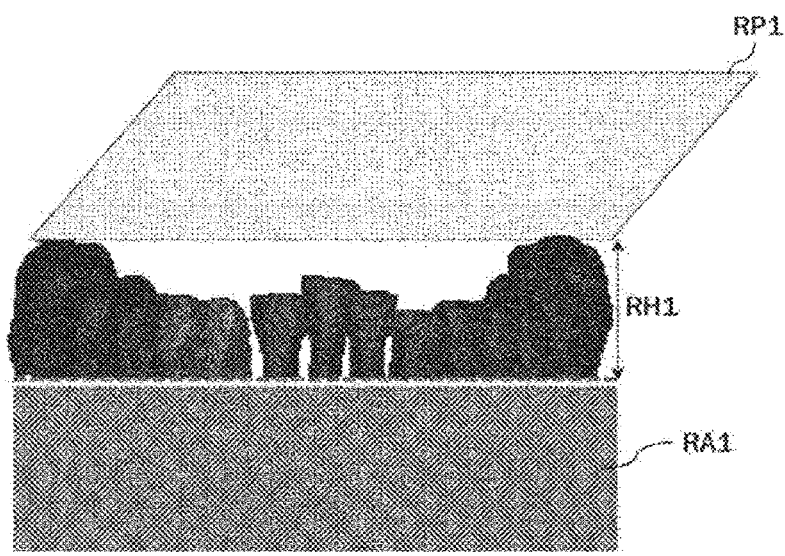

FIGS. 15 and 16 are exemplary views for explaining a preprocessing method when a flat reference plane RP1 is applied.

Referring to FIGS. 15 and 16, the reference plane RP may be a plane RP1. In this case, two different reference planes RP1 may be set for the maxilla and mandible.

To this end, the reference plane extraction unit 157 may set a plane at heights EH1 and EH2 of the mandibular outermost teeth ET1 and ET2 (e.g., molars or wisdom teeth, etc.) or at a height spaced apart from the heights EH1 and EH2 by a predetermined height as the reference plane RP1 for the mandible. That is, the reference plane RP1 for the mandible may be a plane passing through the heights EH1 and EH2 of one end of the two mandibular outermost teeth ET1 and ET2, or a plane passing through a height spaced apart from the heights EH1 and EH2 by a predetermined height.

Similarly, the reference plane extraction unit 157 may set a plane at heights of the maxillary outermost teeth or at a height spaced apart from it by a predetermined height as the reference plane RP1 for the maxilla.

Then, referring to FIG. 16, the area setting unit 158 sets an area (checkered area) spaced downward by a predetermined height RH1 from the reference plane RP1 for the mandible as the dental root area RA for the mandible of the CT image.

Similarly, the area setting unit 158 may set an area spaced upward by a predetermined height from the reference plane RP1 for the maxilla as the dental root area RA for the maxilla of the CT image.

However, the separation distance RH1 from the reference plane RP1 for the mandible and the separation distance from the reference plane RP1 for the maxilla set by the area setting unit 158 may be different from each other. This is because the average height of the maxillary teeth and the mandibular teeth may be different from each other.

Figure 17:
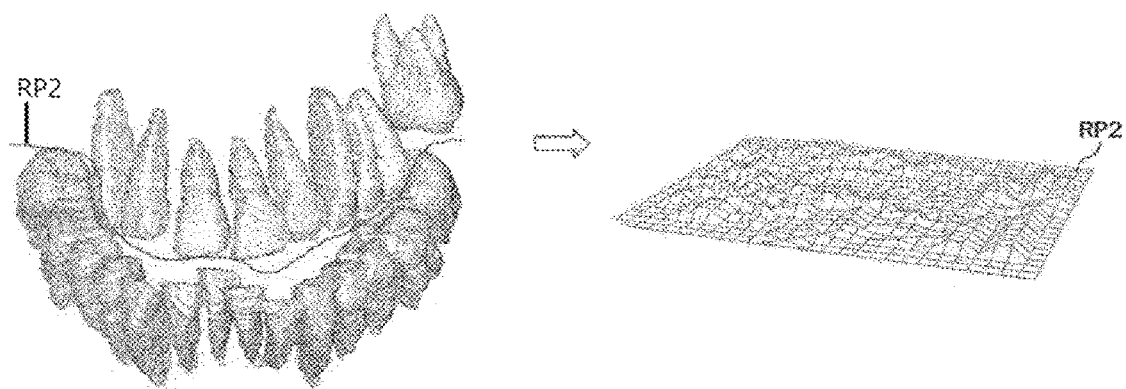
FIGS. 17 and 18 are exemplary views for explaining a preprocessing method when a reference plane RP2 having a three-dimensional boundary surface is applied.
Figure 18:
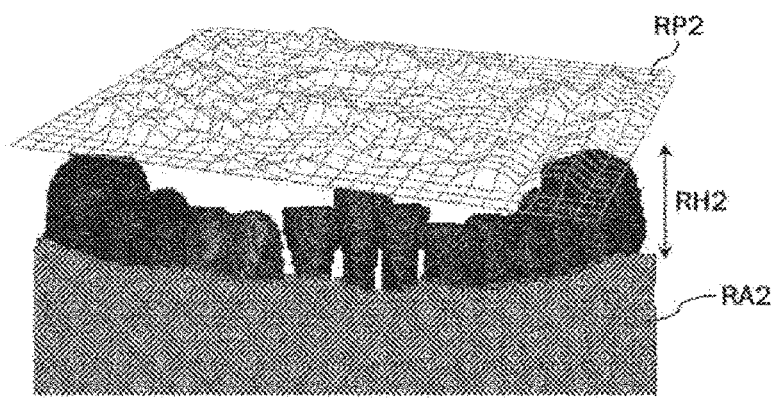

FIGS. 17 and 18 are exemplary views for explaining a preprocessing method when a reference plane RP2 having a three-dimensional boundary surface is applied.

Referring to FIGS. 17 and 18, the reference plane RP may be a three-dimensional boundary surface RP2. In this case, the same one reference plane RP2 may be set or two different reference planes RP2 may be set for the maxilla and the mandible.

First, a case in which the reference plane RP2 of the one same three-dimensional boundary surface is set for the maxilla and the mandible will be described.

That is, the reference plane extraction unit 157 may set a three-dimensional boundary surface that is located in the space between the maxillary teeth and the mandibular teeth (hereinafter referred to as an "interspace") in the CT image and reflects each height of the maxillary teeth and each height of the mandibular teeth, as a reference plane RP2 of the CT image. In this case, the interspace is formed between a three-dimensional boundary surface of a shape corresponding to the ends of the maxillary teeth (hereinafter, referred to as an "upper three-dimensional boundary surface") and a three-dimensional boundary surface of a shape corresponding to the ends of the mandibular teeth (hereinafter, referred to as an "lower three-dimensional boundary surface").

Accordingly, the reference plane extraction unit 157 may set a three-dimensional boundary surface composed of the average height values of the upper three-dimensional boundary surface, the lower three-dimensional boundary surface, or the upper three-dimensional boundary surface and the lower three-dimensional boundary surface as a reference plane RP2.

Then, referring to FIG. 18, the area setting unit 158 sets an area (checkered area) spaced downward by a predetermined height RH2 from the reference plane RP2 as the dental root area RA for the mandible of the CT image. Similarly, the area setting unit 158 may set an area spaced upward by a predetermined height from the reference plane RP2 as the dental root area RA for the maxilla of the CT image.

However, the separation distance RH2 from the reference plane RP2 for setting the dental root area RA for the mandible and the separation distance from the reference plane RP2 for setting the dental root area RA for the maxilla set by the area setting unit 158 may be different from each other. This is because the average height of the maxillary teeth and the mandibular teeth may be different from each other.

Next, a case in which the reference plane RP2 of the two different three-dimensional boundary surfaces is set for the maxilla and the mandible will be described.

That is, the reference plane extraction unit 157 may set the lower three-dimensional boundary surface as the reference plane RA2 for the mandible and the upper three-dimensional boundary surface as the reference plane for the maxilla, respectively.

Then, referring to FIG. 18, the area setting unit 158 sets an area (checkered area) spaced downward by a predetermined height RH2 from the reference plane RP2 for the mandible as the dental root area RA for the mandible of the CT image. Similarly, the area setting unit 158 may set an area spaced upward by a predetermined height from the reference plane RP2 for the maxilla as the dental root area RA for the maxilla of the CT image.

However, the separation distance RH2 from the reference plane RP2 for setting the dental root area RA for the mandible and the separation distance from the reference plane RP2 for setting the dental root area RA for the maxilla set by the area setting unit 158 may be different from each other. This is because the average height of the maxillary teeth and the mandibular teeth may be different from each other.

The apparatus 100 for preprocessing image data according to an exemplary embodiment of the present invention may be manufactured as a separate apparatus or may be included in an image registration apparatus.

After the operation of the apparatus 100 for preprocessing image data according to an exemplary embodiment of the present invention, the image registration apparatus may register the oral scan image from which the gum area is removed and the CT image from which the dental root area RA is removed. Accordingly, the registration speed and the registration accuracy can be improved.

In the detailed description of the present invention, although specific embodiments have been described, it is apparent that various modifications are possible without departing from the scope of the present invention. Therefore, the scope of the present invention is not limited to the described embodiments, and should be defined by the following claims and their equivalents.

The apparatus for preprocessing image data according to the present invention may be used in various dental treatment fields such as implant operation.

What is claimed is:

1. An apparatus for preprocessing image data for image registration, the apparatus comprising a controller, the controller is configured to:
   reduce a mesh resolution of an oral scan image to a reference resolution;
   detect, from the preprocessed oral scan image, a start line corresponding to a bottom of a gum area;
   calculate a maximum curvature and a minimum curvature between adjacent meshes of the oral scan image, and calculates at least one of a Gaussian curvature and an average curvature by using the calculated maximum and minimum curvatures;
   select meshes having at least any one of the calculated Gaussian curvature and the average curvature equal to or greater than a reference curvature, and determines a vertex shared by the selected meshes as a boundary point;
   detect, from the preprocessed oral scan image, a boundary line between a dental area and a gum area; and
   separate a gum area from the oral scan image by using the start line and the boundary line.

2. The apparatus of claim 1, wherein the controller is configured to calculate the number of adjacent vertexes for each mesh of the oral scan image, selects vertexes having the calculated number of vertexes equal to or less than a reference number, and detects the start line by connecting the selected vertexes.

3. The apparatus of claim 1, wherein the controller is configured to calculate a curvature of each mesh of the oral scan image, selects meshes having the calculated curvature equal to or less than a reference curvature, and detects the start line by connecting the vertexes included in the selected meshes.

4. The apparatus of claim 1, wherein the controller is configured to calculate a curvature between adjacent meshes of the oral scan image, selects meshes having the calculated curvature equal to or greater than a reference curvature, and determines a vertex shared by the selected meshes as a boundary point.

5. The apparatus of claim 4, wherein the controller is configured to connect the adjacent boundary points by sequentially dilating and eroding the boundary points.

6. The apparatus of claim 1, wherein the controller is configured to connect the adjacent boundary points by sequentially dilating and eroding the boundary points.

7. The apparatus of claim 6, wherein the controller is configured to label each of the connected boundary points with the same label.

8. The apparatus of claim 7, wherein the controller is configured to dilate at least once for each labeled label, and integrates adjacent labels.

9. The apparatus of claim 1, wherein the controller is configured to integrate vertexes connected from the start line to the boundary line and setting it as a separation target area.

10. The apparatus of claim 9, wherein the controller is configured to determine the outermost line of the separation target area as a separation reference line for separating a gum area from the oral scan image.

11. The apparatus of claim 10, wherein the controller is configured to separate a gum area from the oral scan image using the separation reference line.

12. The apparatus of claim 1, the controller is configured to:
    extract a reference plane from a CT image;
    set an area spaced apart by a predetermined height from the reference plane as a dental root area; and
    process the CT image data so that the dental root area is removed from the CT image.

13. The apparatus of claim 12, wherein the controller is configured to set a plane at heights of the maxillary outermost teeth or at a height spaced apart from it by a predetermined height as a reference plane for the maxilla, and sets a plane at heights of the mandibular outermost teeth or at a height spaced apart from it by a predetermined height as a reference plane for the mandible, respectively.

14. The apparatus of claim 12, wherein the controller is configured to extract a three-dimensional boundary surface that is located in a space between the maxillary teeth and the mandibular teeth and reflects heights of the maxillary teeth and the mandibular teeth, as a reference plane.

15. The apparatus of claim 12, wherein the controller is configured to set a three-dimensional boundary surface corresponding to a shape of ends of maxillary teeth as a reference plane for the maxilla, and a three-dimensional boundary surface corresponding to a shape of ends of mandibular teeth as a reference plane for the mandible, respectively.

* * * * *